United States Patent [19]

Sakamoto

[11] Patent Number: 5,144,013

[45] Date of Patent: Sep. 1, 1992

[54] BODY FLUID PURIFYING MATERIAL AND METHOD FOR PURIFYING BODY FLUID BY USE THEREOF

[75] Inventor: Nagayoshi Sakamoto, Ichihara, Japan

[73] Assignee: Ube Industries, Ltd., Yamaguchi, Japan

[21] Appl. No.: 810,303

[22] Filed: Dec. 19, 1991

Related U.S. Application Data

[63] Continuation of Ser. No. 613,960, Nov. 13, 1990, abandoned, which is a continuation of Ser. No. 97,956, Sep. 17, 1987, abandoned.

[30] Foreign Application Priority Data

Sep. 24, 1986 [JP] Japan ............... 61-223653
Sep. 24, 1986 [JP] Japan ............... 61-223654
Jul. 30, 1987 [JP] Japan ............... 62-189009
Jul. 30, 1987 [JP] Japan ............... 62-189010

[51] Int. Cl.$^5$ ............... C07K 17/10; C08B 37/12; C08B 15/06; C08B 37/02
[52] U.S. Cl. ............... 530/415; 536/1.1; 536/3; 536/20; 536/30; 536/51; 604/2; 604/416; 527/301; 435/2
[58] Field of Search ............... 536/1.1, 3, 20, 30, 536/51; 604/2, 416; 527/301; 435/2; 530/415

[56] References Cited

U.S. PATENT DOCUMENTS

| | | | |
|---|---|---|---|
| 3,860,573 | 1/1975 | Honkanen et al. | 536/51 |
| 3,873,514 | 3/1975 | Chu et al. | 536/3 |
| 3,959,251 | 5/1976 | Porath et al. | 536/1.1 |
| 4,004,979 | 1/1977 | Aurameas et al. | 435/176 |
| 4,108,975 | 8/1978 | Hales | 436/500 |
| 4,152,170 | 5/1979 | Nagase et al. | 536/1.1 |
| 4,172,071 | 10/1979 | De Maeyer et al. | 530/413 |
| 4,177,038 | 12/1979 | Biebricher et al. | 435/179 |
| 4,195,127 | 3/1980 | Hartdegen et al. | 435/174 |
| 4,319,976 | 3/1982 | Gurske | 536/3 |
| 4,464,468 | 8/1984 | Avrameas et al. | 435/177 |
| 4,605,394 | 8/1986 | Skurkovich | 604/4 |
| 4,708,714 | 11/1987 | Larsson et al. | 604/5 |
| 4,716,219 | 12/1987 | Eggimann et al. | 536/1.1 |
| 4,775,482 | 10/1988 | Thurman | 604/5 |
| 4,791,068 | 12/1988 | Loskutoff et al. | 436/518 |

FOREIGN PATENT DOCUMENTS

| | | |
|---|---|---|
| 0082345 | 6/1983 | European Pat. Off. |
| 0109531 | 5/1984 | European Pat. Off. |
| 0111696 | 6/1984 | European Pat. Off. |
| 54-135497 | 10/1979 | Japan |
| 62-192172 | 8/1987 | Japan |
| 62-270602 | 11/1987 | Japan |
| 1222949 | 2/1971 | United Kingdom |

OTHER PUBLICATIONS

Friesen et al.; Vox Sang. 48:201-212 (1985).
Marcus et al.; American Heart Journal 110 (1, p&1):30-39, Jul. 1985.
Avrameas et al.; Chemical Abstracts 72:63566w (1970).
Péterfy et al.; Ann. Immunol. Hung. 18:85-92 (1976).
Yabe et al.; Chemical Abstracts 107:129973b (1987).
Fei et al.; Biomat., Art. Cells, Art. Org., 15(1):215-228 (1987).
Bamford et al.; Polymer Journal 19(5):475-483 (1987).

*Primary Examiner*—Ronald W. Griffin
*Assistant Examiner*—Nancy S. Carson
*Attorney, Agent, or Firm*—Frishauf, Holtz, Goodman & Woodward

[57] ABSTRACT

There are disclosed a body fluid purifying material which comprises a water-insoluble compound obtained by allowing one or more kinds of a polymeric compound having hydroxyl groups to react with a compound having at least one isocyanate group, and a method for purifying a body fluid which comprises using a water-insoluble polymeric compound obtained by allowing one or more kinds of a polymeric compound having hydroxyl groups to react with a compound having at least one isocyanate compound.

4 Claims, No Drawings

BODY FLUID PURIFYING MATERIAL AND METHOD FOR PURIFYING BODY FLUID BY USE THEREOF

This application is a continuation of application Ser. No. 07/613,960, filed Nov. 13, 1990, abandoned, which is a continuation of application U.S. Ser. No. 07/097,956, filed Sep. 17, 1987, abandoned.

BACKGROUND OF THE INVENTION

This invention relates to a body fluid purifying material, to a method for purifying a body fluid by use thereof and to a method for removing organ transplantation rejection factors exhibited in blood.

With progress of medicine, it has become possible to transplant organs such as heart, kidney and liver, but it is a task of crucial importance to inhibit or alleviate the rejection reactions accompanied with organ transplantation. In the prior art, medicaments such as cyclosporin, azathiopurine, etc. have been administered for the purpose of inhibiting rejection reactions, but sufficient care should be paid to the dose of those medicaments because of the side effect possessed by such medicaments.

Various factors are involved in rejection reaction during organ transplantation. Concerning kidney transplantation having many practical cases among organ transplantation of human being, the rejection phenomenon after kidney transplantation has been said to be frequently caused by the immunological reaction which occurs after the lymphocytes of the recipient recognize the doner antigen released from the transplanted kidney as the non-self foreign antigen. For example, when kidney transplantation is performed, anti-T-cell antibody which is deemed to be the important factor for the rejection reaction, particularly important anti-T-warm antibody, is generated in the plasma of the patient. Therefore, if this factor can be removed, the rejection reaction can be inhibited or alleviated.

Plasma exchange has been practiced for the purpose of removing organ transplantation rejection factors to give considerable effects. Plasma exchange therapeutical method is now being widely used as therapeutical means for serious diseases such as chronic rheumatic arthritis, myasthenia gravis, systemic lupus erythematosus (SLE), fulminant hepatitis, posttransfusion purpura, hyperviscosity syndrome, medicament intoxication, thrombotic thrombocytopenic purpura, blood type incompatible pregnancy, sickel cell anemia, acute progressive glomerular nephritis accompanied with vessel inflammation, chronic liver failure, thrombocytosis, cryoglobulinemia, kidney failure by multiple myeloma, cancer, familial hypercholesterolemia, etc.

However, in the plasma exchange therapeutical method, 2 to 4 liters of plasma are required for plasma exchange for one time, and it is very difficult to procure persistently such amount of plasma or albumin.

Under such background, it has been investigated and practiced to purify the plasma separated from a patient and return the purified plasma again into the body of the patient. As one of such methods, there is the method in which hollow fibers of an organic polymeric compound are used. However, this method sieves the plasma components only according to the sizes of molecules, and also removes active ingredients, and also has the drawback that fluctuation of the components removed may be caused by clogging.

Also, the plasma purifying method by use of an adsorbent has been investigated and applied clinically. As the adsorbent for removing unnecessary factors in plasma, there may be included, for example, protein A-supporting adsorbent, DNA-supporting adsorbent, tryptophan-supporting adsorbent, methylated albumin-supporting adsorbent, heparin-supporting adsorbent, etc. Among them, those derived from living body, such as protein A-supporting adsorbent, DNA-supporting adsorbent, although excellent in adsorption specificity, have the drawback that lowering in adsorption characteristic will be brought about during sterilization, storage or manufacture. Also, in the adsorbent using an antigen or antibody as the ligand, when the ligand is eliminated from the adsorbent, an immune complex is formed, whereby there is the fear that side effect may be brought about. For such reasons, adsorbents with the use of physiological polymeric material derived from living body as the ligand have many problem in practical application.

Further, as the method for purifying plasma in general, there are the methods to use hollow fibers or adsorbents as mentioned above, but they have not been used for the purpose of removing organ transplantation rejection factors, and also there is not report at all about selective removal of anti-T-cell antibody with an adsorbent.

SUMMARY OF THE INVENTION

An object of the present invention is to provide a body fluid purifying material, a method for purifying a body fluid by use thereof and a method for removing organ transplantation rejection factors exhibited in blood.

The body fluid purifying material of the present invention comprises a water-insoluble polymeric compound obtained by allowing one or two or more kinds of a polymeric compound having hydroxyl groups to react with a compound having an isocyanate group or groups.

Further, the present invention concerns a method for removing organ transplantation rejection factors, which comprises bringing the blood of an organ transplantation patient or the plasma separated from said blood into contact with an adsorbent, thereby adsorbing and removing anti-T-cell antibody.

DESCRIPTION OF THE PREFERRED EMBODIMENTS

The polymeric compound having hydroxyl groups to be used in the present invention may include, for example, agarose, cellulose, dextran, chitin, chitosan, polyvinyl alcohol or a compound represented by the following formula (I):

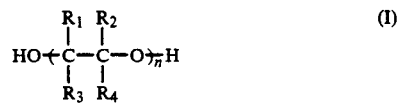

wherein $R_1$, $R_2$, $R_3$ and $R_4$ each independently represent a hydrogen atom or an alkyl group having 1 to 3 carbon atoms, and n represents an integer of 10 to 200, and these can be used either singly or as a mixture of two or more compounds, but it is preferable to use a crosslinked compound.

As the compound represented by the above formula (I), for example, polyethylene glycol, polypropylene glycol, and poly(1,2-butanediol) may be included. In the above formula (I), compounds with n being 10 to 200 correspond to those having average molecular weights of 500 to 50,000. As such compounds, those with n of 40 to 100 in the above formula (average molecular weight of 2,000 to 20,000) are particularly preferred.

Examples of compounds having an isocyanate group or groups may include monofunctional isocyanate group such as methyl isocyanate, ethyl isocyanate, propyl isocyanate, butyl isocyanate, octyl isocyanate, decyl isocyanate, octadecyl isocyanate, phenyl isocyanate, tolyl isocyanate, naphthyl isocyanate, etc.; bifunctional isocyanates represented by the following formula (II):

OCN—R—NCO　　　　　　　　　　(II)

wherein R represents an aliphatic chain having 2 to 12 carbon atoms or an aromatic chain having 6 to 15 carbon atoms; and polyisocyanates having trifunctional or more groups. Difunctional isocyanates may include, for example, hexamethylene diisocyanate, tetramethylene diisocyanate, o-toluidine isocyanate, toluylene diisocyanate, naphthylene-1,5-diisocyanate, 4,4'-diphenylmethane diisocyanate, and polyfunctional isocyanate may be, for example, triphenylmethane-4,4',4''-triisocyanate.

As the water-insoluble polymeric compound for the body fluid purifying material of the present invention, a reaction product of a cross-linked agarose and hexamethylene diisocyante is preferred. Also, it is preferable to use a water-insoluble polymeric compound which is obtained by the reaction between a compound having two or more isocyanate groups in the molecule and a polymeric compound having hydroxyl groups, followed subsequently by the reaction with a polymeric compound having hydroxyl groups, particularly the compound represented by the above formula (I). As such compounds, those obtained by subjecting the reaction product of cross-linked agarose and hexamethylene diisocyanate to the reaction with polyethylene glycols may be included.

The water-insoluble polymeric compound for the body fluid purifying material of the present invention should preferably contain a nitrogen content under dry state of 3.0 to 9.0% by weight, more preferably 4.5 to 5.5% by weight. The materials with the nitrogen content in such range will best adsorb unnecessary factors in body fluid The water-insoluble polymeric compound for the body fluid purifying material of the present invention can be prepared, for example, as follows As the polymeric compound having hydroxyl groups, originally those under dry state are used. When said polymeric compound contains water, it may be subjected to drying by conventional means such as freeze-drying under reduced pressure, drying under reduced pressure, etc., or repeated replacement treatment with anhydrous organic solvents before use. The organic solvent to be used for replacement may be generally the solvent to be used for the reaction, as exemplified by dimethyl sulfoxide, dimethylacetamide, dimethylformamide, tetrahydrofuran, acetone, methyl ethyl ketone, methyl isobutyl ketone.

The reaction may be carried out by suspending or dissolving a polymeric compound having hydroxyl groups in an organic solvent and adding a compound having an isocyanate group or groups, generally at 10° to 200° C., preferably 30° to 110° C., under stirring. The organic solvent to be used in the reaction may be employed as the same ones used in the above replacement treatment. In this case, the ratio of the hydroxyl groups (—OH) present in the polymeric compound having hydroxyl groups to the isocyanate groups (—NCO) present in the compound having an isocyanate group or groups is not particularly limited, but the —NCO/—OH (molar ratio) may be preferably 1 or more.

When a polymeric compound having hydroxyl groups, particularly the compound represented by the above formula (I) is allowed to react subsequently to the reaction of the compound having two or more isocyanate groups in the molecule with the polymeric compound having hydroxyl groups to obtain a water-insoluble polymeric compound, the following procedure may be practiced.

After the reaction between the hydroxyl groups and isocyanate groups by stirring for a predetermined time, for the purpose of removing excessive and unreacted isocyanate compounds and other by-products, the reaction product is washed with a solvent repeatedly. After confirmation that no isocyanate compound is contained in the washing, the polymeric compound having hydroxyl group as mentioned above, particularly the compound represented by the above formula (I) is added into the system comprising the reaction product and the solvent, and the reaction is carried out generally at 10° to 200° C. preferably 50° to 110° C., under stirring The above reactions are all conducted under the conditions in absence of moisture in the reaction system.

After completion of the reaction, remaining isocyanate groups are deactivated by addition of an amine, an alcohol or water into the reaction system.

Available amines may include methylamine, ethylamine, butylamine, diethylamine, ethanolamine and the like, and available alcohols may include methanol, ethanol, propanol, butanol and the like, but they are not limitative of the present invention.

In the case of monoisocyanate, it is washed away when remained in the system, and therefore no deactivation treatment is generally required. However, it may be also treated with amines, alcohols as mentioned above or water.

After suction filtration of the reaction product, it is added into a reaction solvent and stirred for a while at ambient temperature to dissolve remainder of unreacted products in the solvent. The reaction product is suction filtered, repeatedly washed with water and ordinarily stored under wet state in physiological saline.

For the reaction products of which isocyanate groups are deactivated with water or alcohol, the water-insoluble polymeric compounds with nitrogen contents under dry state of 3.0 to 8.0% by weight, particularly 4.5 to 5.5% by weight, can well adsorb unnecessary factors in body fluid, and for the reaction products of which isocyanate groups are deactivated with amine, the nitrogen content may be preferably 3.5 to 9.0% by weight under dry state.

The body fluid purifying material of the present invention comprises such a water-insoluble polymeric compound, and its shape is not particularly limited, including particulate, fibrous, film, hollow fiber shapes, etc., but particulate and fibrous shapes are preferred for easiness in handling In the case of particulate shapes, the particle sizes may be generally 10 to 5,000 μm, preferably 50 to 1,000 μm, in aspect of clogging and adsorption speed of the adsorbed materials when filled in a column, but these are not limitative of the present invention.

Also, in the case of spherical cross-linked product, a highly hydrous product wetted with water to a water content of 50 to 95% is preferred.

Also, the body fluid purifying material of the present invention can be sterilized according to such methods as high pressure steam sterilization, EOG sterilization, γ-ray irradiation sterilization, etc.

Further, the present invention is inclusive of the method for purifying a body fluid by use of the above body fluid purifying material.

As a specific example of the method for purifying a body fluid, the following method may be included. For example, in the case of blood, a plasma separated by centrifugal separation or membrane separation is passed through a column filled with the material according to the present invention. Alternatively, the plasma and the body fluid purifying material of the present invention are stirred for a predetermined time in a vessel, followed by filtration of the plasma. In both column passage and batch, the temperature may be 10° to 42° C., preferably 25° to 37° C. The plasma separated by plasma separator is pooled and can be purified by either column passage or the batch method, but it is pratically preferred to be continuously passed through a column and returned again into body.

The blood purifying material of the present invention is also capable of purification by use of whole blood When the blood purifying material of the present invention is used, immonoglobulins, IgG of multiple myeloma patient, immune complexes, rheumatoid factors, etc. can be well removed by adsorption, and further rejection reaction factors formed in the body of an organ transplantation patient can be well removed by adsorption Particularly, in a kidney transplantation patient, anti-T-cell antibody (anti-T warm antibody) which is the rejection reaction factor, can be effectively removed.

In the case of removing organ transplantation rejection factors by use of such an adsorbent, for example, the following method may be applicable.

First, the adsorbent is filled in a cylindrical column made of a plastic with an inner volume of 200 to 500 ml, and the inlet and the outlet for passage of blood are provided with filters for prevention of outflow of the adsorbent. The filters may be provided as double structures or more, if necessary. The material, shape, volume of the column are not limited to those as described above. For example, in order to make contact of blood with the adsorbent more frequent, the column may be made to have internally a honeycomb structure. The adsorbent is required to be sterilized by such method as high pressure steam pressurization, EOG sterilization, γ-ray irradiation sterilization, either previously or after filled in the column. Subsequently, the blood sampled from an organ transplanted patient or the plasma separated from the above blood by centrifugation or membrane separation is passed through the column filled with the above adsorbent. Also, other than the column method, the batch method, in which the blood or plasma and the above adsorbent are placed in a vessel, stirred for a predetermined time and then the plasma is filtered, is also applicable. In either the column method or the batch method, the operation is practiced generally at 10° to 42° C., preferably at 25° to 37° C. The blood or the plasma separated by a plasma separator may be pooled and purified according to the column method or the batch method, but it is practically preferably continuously passed through a column and returned again into the body.

The method of the present invention is useful as the method for removing organ transplantation rejection factors in blood or plasma of a patient whose organ such as kidney, heart, liver, pancreas, etc., is to be transplanted.

Also, anti-DNA antibody and immune complex in a plasma of a systemic lupus erythematosus and anti-thyroglobulin antibody and anti-thyroid microsome antibody in a patient of Hashimoto's disease can be well removed by adsorption.

Also, in the blood of a cancer patient, immune inhibiting factor is generated and immune action of the patient will be lowered as it is increased, and the body fluid purifying material of the present invention can also remove by adsorption the immune inhibiting factor generated in the blood of a cancer patient.

Further, it can also remove by adsorption the AIDS virus (HIV) in the blood of an AIDS (acquired immunodeficiency syndrome) patient.

EXAMPLES

The present invention is described in detail below by referring to Examples, but these Examples do not limit the scope of the present invention at all.

EXAMPLE 1

Preparation of body fluid purifying material (1) A cross-linked agarose [trade name: Sepharose CL-4B, produced by Pharmacia Co.] was washed repeatedly with distilled water, and water was completely squeezed off by suction filtration. An amount of 20.0 g of the cross-linked agarose under wet state (1.54 g under absolute dry state) was added into 250 ml of dehydrated dimethyl sulfoxide (hereinafter called "DMSO") and the mixture was stirred at ambient temperature for 2 hours. After DMSO was removed in a system in absence of moisture, 100 ml of dehydrated DMSO was freshly added, followed by stirring at ambient temperature for 4 hours. Subsequently, the operations of 100 ml (10 hours), 50 ml (2 hours) were repeated similarly, followed finally by addition of 50 ml of DMSO. The water content in DMSO in the system was analyzed by the Karl Fischer method to be 10 ppm or less Into this system was charged a solution of 2.5 g of hexamethylene diisocyanate (hereinafter called "HMDI") added into 20 ml of DMSO, and the reaction was carried out by stirring at 100° C. for 3 hours. After removal of the reaction solvent, 70 ml of fresh DMSO was charged and washing was performed by stirring at ambient temperature for 2 hours. Subsequently, washing was successively performed similarly under the conditions of 50 ml (2 hours), 50 ml (1 hour), 50 ml (3 hours) and 50 ml (5 hours). When the isocyanate group in 50 ml of the final washing was analyzed by titration, no isocyanate group was detected. The reaction product was divided into 3 equal portions, to each of which was added 50 ml of dehydrated DMSO, and further ethanolamine (5 ml), ethanol (10 ml) and water (10 ml) were respectively added, followed by stirring (90° C., 2 hours). The reaction product was washed with a large amount of water and confirmed to be free from eluted product, and then sterilized under steam pressure at 121° C. for 30 minutes before storage under wet state (physiological saline).

The products prepared according to the above methods are called body fluid purifying material A (ethanolamine treated product), body fluid purifying material B (ethanol treated product) and body fluid purifying material C (water treated product), respectively.

(2) A cross-linked dextran [trade name: Sephadex, produced by Pharmacia Co.] was washed repeatedly with distilled water, and water was completely squeezed off by suction filtration An amount of 150.0 g of the thus obtained cross-linked dextran under wet state was freeze-dried (weight after freeze-drying: 6.83 g). The freeze-dried cross-linked dextran (5.0 g) was added into 150 ml of dehydrated dimethylacetamide (hereinafter called "DMAA") and further into the system was charged a solution of 4.0 g of HMDI added into 30 ml of dehydrated DMAA, and the reaction was carried out under stirring at 80° C. for 5 hours. After removal of the reaction solvent by suction filtration at ambient temperature under dry atmosphere, 200 ml of fresh DMAA was charged, and washing was performed under stirring at ambient temperature for 1 hour. Subsequently, washing was performed similarly for 5 times under the conditions of 200 ml (2 hours) DMAA. When the isocyanate group in 70 ml of the final washing was analyzed by titration, no isocyanate group was detected. The reaction product was divided into 3 equal portions, to each of which was added 50 ml of dehydrated DMAA, and further ethylamine (10 ml), propanol (10 ml) and water (10 ml) were added respectively, followed by stirring (80° C., 2 hours). The reaction product was washed with a large amount of water and confirmed to be free from eluted product, and sterilized under steam pressure at 121° C. for 30 minutes before storage under wet state (physiological saline).

The products prepared according to the above method are called body fluid purifying material D (ethylamine treated product), body fluid purifying material E (propanol treated product) and body fluid purifying material F (water treated product), respectively.

(3) A cross-linked agarose [trade name: Sepharose CL-4B, produced by Pharmacia Co.] was washed repeatedly with distilled water, and water was completely squeezed off by suction filtration. An amount of 153.0 g of the thus obtained cross-linked agarose under wet state (9.2 g under absolute dry state) was added into 300 ml of dehydrated DMSO and the mixture was stirred at ambient temperature for 3 hours. After DMSO was removed in a system in absence of moisture, 200 ml of dehydrated DMSO was freshly added, followed by stirring at ambient temperature for 7 hours Subsequently, the operations of 160 ml (12 hours), 150 ml (12 hours), 140 ml (12 hours), 160 ml (12 hours) and 140 ml (12 hours) were repeated similarly, followed finally by addition of 50 ml of DMSO. The water content in DMSO in the system was analyzed by the Karl Fischer method to be 10 ppm or less Into this system was charged a solution of 11.4 g of HMDI added into 50 ml of DMSO, and the reaction was carried out by stirring at 100° C. for 2 hours After removal of the reaction solvent, 300 ml of fresh DMSO was charged and washing was performed by stirring at ambient temperature for 2 hours. Subsequently, washing was successively performed similarly under the conditions of 300 ml (2 hours) with fourth times. An amount of the isocyanate group in the final washing solution (300 ml) was determined by the tritration method but no isocyanate group was detected. Subsequently, 300 ml of dehydrated DMSO and 60 g of polyethylene glycol having an average molecular weight of 6,000 were charged thereto and reaction was carried out at 100° C. for 90 minutes under stirring. Then, the reaction product was divided into 3 equal portions, ethanolamine (10 ml), ethanol (10 ml) and water (10 ml) were respectively added, followed by stirring (90° C., 2 hours). The reaction product was washed with a large amount of water and confirmed to be free from eluted product, and then sterilized under steam pressure at 121° C. for 30 minutes before storage under wet state (physiological saline).

The products prepared according to the above method are called body fluid purifying material G (ethylamine treated product), body fluid purifying material H (propanol treated product) and body fluid purifying material I (water treated product), respectively.

Adsorption test (1) A glass column of 10 mm inner diameter was filled with each body fluid purifying material of the present invention as prepared above, and the column was equipped at the inlet and the outlet with filters of 50 micron mesh. The plasma employed was separated from the patient after plasma exchange after kidney transplantation The total amount of the plasma passed through the adsorption apparatus was 28 ml, with the plasma circulation rate being 0.3 ml/min. and the column temperature 37° C. By varying variously the body fluid purifying material amount and the circulation time, the flowing adsorption tests were conducted and thereafter the total protein (hereinafter called "TP"), albumin (hereinafter called "AL"), IgG and anti-T-cell antibody and anti-B-cell antibody were analyzed TP was measured by the biurette method, AL by the BCG method, IgG by the one-dimensional radioimmunodiffusion method, anti-T-cell antibody and anti-B-cell antibody by the CDC (Complement-dependent cytotoxicity) test.

The results are shown in Table 1. As is apparent from this Table, when the body fluid purifying materials A to I according to the present invention are used, it can be understood that, in the antibody to donor lymphocytes, T-warm becomes smaller than the score 8 to remove by adsorption the anti-T-warm antibodies which appeared during kidney transplantation. In all of the present adsorption tests, no great pressure loss through column passage occurred (in most cases, pressure loss was 0 to 5 mm Hg).

TABLE 1

| Kind of fluid purifying material | Amount of body fluid purifying material [ml (wet)] | Plasma circuration time (min) | TP (g/dl) | AL (g/dl) | IgG (mg/dl) | Anti-T-cell antibody* | | | Anti-B-cell antibody* | | |
|---|---|---|---|---|---|---|---|---|---|---|---|
| | | | | | | 5° C. | room temperature | 37° C. | 5° C. | room temperature | 37° C. |
| — | None | 0 | 5.7 | 4.8 | 576 | 8 | 8 | 8 | 8 | 8 | 8 |
| | | | | | | 8 | 8 | 8 | 8 | 8 | 8 |
| — | None | 120 | 5.7 | 4.8 | 576 | 8 | 8 | 8 | 8 | 8 | 8 |
| | | | | | | 8 | 8 | 8 | 8 | 8 | 8 |
| A | 5 | 60 | 5.1 | 4.4 | 380 | 4 | 4 | 4 | 8 | 8 | 8 |

TABLE 1-continued

| Kind of fluid purifying material | Amount of body fluid purifying material [ml (wet)] | Plasma circu- ration time (min) | TP (g/dl) | AL (g/dl) | IgG (mg/dl) | Anti-T-cell antibody* | | | Anti-B-cell antibody* | | |
|---|---|---|---|---|---|---|---|---|---|---|---|
| | | | | | | 5° C. | room temper- ature | 37° C. | 5° C. | room temper- ature | 37° C. |
| | 5 | 120 | 4.8 | 4.3 | 325 | 4 4 | 4 4 | 4 4 | 8 8 | 8 6 | 8 6 |
| B | 5 | 60 | 5.0 | 4.5 | 363 | 4 4 | 4 4 | 4 4 | 8 8 | 8 8 | 8 8 |
| | 5 | 120 | 4.8 | 4.3 | 330 | 4 4 | 4 4 | 4 4 | 8 8 | 8 6 | 8 6 |
| C | 5 | 60 | 4.9 | 4.4 | 350 | 4 4 | 4 2 | 4 2 | 8 8 | 8 6 | 6 6 |
| | 5 | 120 | 4.8 | 4.2 | 312 | 4 4 | 4 2 | 4 2 | 2 8 | 8 6 | 6 6 |
| D | 5 | 120 | 4.9 | 4.3 | 384 | 4 4 | 4 4 | 4 4 | 8 8 | 8 8 | 8 8 |
| E | 5 | 120 | 4.9 | 4.3 | 398 | 4 4 | 4 4 | 4 4 | 8 8 | 8 6 | 8 6 |
| F | 5 | 120 | 4.9 | 4.2 | 370 | 4 4 | 4 4 | 4 2 | 8 8 | 8 8 | 8 6 |
| G | 3 | 60 | 5.0 | 4.3 | 184 | 1 1 | 1 1 | 1 1 | 8 8 | 8 8 | 1 1 |
| | 5 | 60 | 5.0 | 4.1 | 132 | 1 1 | 1 1 | 1 1 | 6 8 | 8 8 | 1 1 |
| | 3 | 120 | 4.8 | 4.0 | 170 | 1 1 | 1 1 | 1 1 | 8 6 | 8 6 | 1 1 |
| | 5 | 120 | 4.9 | 4.0 | 128 | 1 1 | 1 1 | 1 1 | 6 8 | 6 8 | 1 1 |
| H | 3 | 60 | 5.1 | 4.2 | 178 | 1 1 | 1 1 | 1 1 | 8 8 | 8 6 | 1 1 |
| | 5 | 60 | 4.9 | 4.2 | 136 | 1 1 | 1 1 | 1 1 | 8 8 | 8 6 | 1 1 |
| | 3 | 120 | 4.7 | 4.1 | 174 | 1 1 | 1 1 | 1 1 | 8 8 | 8 6 | 1 1 |
| | 5 | 120 | 4.8 | 4.1 | 115 | 1 1 | 1 1 | 1 1 | 8 8 | 6 6 | 1 1 |
| I | 3 | 60 | 5.2 | 4.3 | 174 | 1 1 | 1 1 | 1 1 | 8 8 | 8 6 | 1 1 |
| | 5 | 60 | 5.1 | 4.2 | 125 | 1 1 | 1 1 | 1 1 | 8 8 | 4 8 | 1 1 |
| | 3 | 120 | 4.9 | 4.2 | 168 | 1 1 | 1 1 | 1 1 | 8 8 | 8 6 | 1 1 |
| | 5 | 120 | 4.8 | 4.2 | 90 | 1 1 | 1 1 | 1 1 | 8 8 | 6 6 | 1 1 |

*representation of score by CDC test.
1: 0 to 10% killed, 2: 11 to 20% killed, 4: 21 to 40% killed, 6: 41 to 80% killed and 8: 81 to 100% killed.

(2) In place of the plasma of the patient after kidney transplantation, a plasma of a multiple myeloma patient was used, and the above adsorption test (1) was conducted under otherwise the same condition to obtain the results as shown in Table 2. However, in this test, no CDC test was conducted for analysis of anti-T-cell antibody and anti-B-cell antibody.

From Table 2, it can be clearly seen that IgG in the plasma of multiple myeloma patient can be well removed by adsorption by use of the body fluid purifying materials A, B, C, D, E and F according to the present invention In all of the present adsorption tests, no great pressure loss by column passage occurred (in most cases, pressure loss was 0 to 5 mm Hg).

TABLE 2

| Kind of body fluid purifying material (symbol) | Amount of body fluid purifying material (wet) | Blood circu- lation time (min) | TP (g/dl) | AL (g/dl) | IgG (mg/dl) |
|---|---|---|---|---|---|
| — | None | 0 | 6.8 | 4.3 | 2580 |
| — | None | 120 | 6.8 | 4.3 | 2580 |
| A | 5 | 120 | 5.0 | 3.4 | 1450 |
| B | 5 | 120 | 4.7 | 3.8 | 1470 |
| C | 5 | 120 | 4.8 | 3.6 | 1390 |
| D | 5 | 120 | 5.0 | 3.6 | 1405 |
| E | 5 | 120 | 5.2 | 3.7 | 1720 |
| F | 5 | 120 | 5.1 | 3.6 | 1680 |

(3) An amount of 0.5 ml of the body fluid purifying material A according to the present invention was added to 1.5 ml of a fresh human plasma, and after shaking stirring at 37° C. for 3 hours, the mixture was centrifuged at 3000 rpm for 15 minutes. The resultant supernatant was analyzed. The results obtained are shown below.

| | TP (g/dl) | AL (g/dl) | IgG (mg/dl) |
|---|---|---|---|
| Before the present adsorption test | 6.5 | 4.2 | 1852 |
| After the present adsorption test | 5.3 | 3.8 | 1138 |

From the above results, it can be appreciated that the body fluid purifying material A according to the present invention can well adsorb IgG.

EXAMPLE 2

Preparation of body fluid purifying material

A cross-linked agarose [trade name: Sepharose CL-4B, produced by Pharmacia Co.] was washed repeatedly with distilled water, and water was completely squeezed off by suction filtration. An amount of 60.0 g of the cross-linked agarose under wet state (4.0 g under absolute dry state) was added into 125 ml of DMSO and the mixture was stirred at ambient temperature for 1 hour. After DMSO was removed in a system in absence of moisture, 100 ml of dehydrated DMSO was freshly added, followed by repetition of similar operations. When the water content in the DMSO in the system became 50 ppm or less, a solution of 2.28 g of HMDI added into 25 ml of dehydrated DMSO was charged into this system, and the reaction was carried out at 100° C. for 1.5 hours under stirring (the amount of DMSO in the reaction system was 125 ml). After removal of the reaction solvent, 200 ml of fresh DMSO was charged and washing was performed by stirring at ambient temperature for 1 hour. Subsequently, washing was repeated until the isocyanate in DMSO in the system became $1 \times 10^{-6}$ equivalent or less by titration analysis. Subsequently, a solution of 30 g of a polyethylene glycol (average molecular weight 6,000, hereinafter called "PEG") dissolved in 200 ml of dehydrated DMSO was charged, and the reaction was carried out at 100° C. for 1.5 hours. The temperature was lowered to room temperature, whereupon 50 ml of water was added and stirring was conducted for 1 hour. The reaction product was washed with a large amount of distilled water and confirmed to be free from eluted product, followed by sterilization by high pressure steam at 121° C. for 30 minutes.

The water-insoluble polymeric compound thus prepared was suction filtered and provided for the following test as body fluid purifying material No. 1. The water containing water-insoluble polymeric compound suction filtered was found to have a water content of 72%, and the dried product thereof had a nitrogen content of 4.68%.

The product prepared according to the above method is called body fluid purifying material J.

Adsorption test (a) The same adsorption test (3) as in Example 1 was conducted except for using the body fluid purifying material No. 1 according to the present invention as prepared above as the body fluid purifying material to obtain the results as shown in Table 3.

(b) A glass column of 10 mm inner diameter was filled with 3 g of the body fluid purifying material No. 1 according to the present invention prepared as described above (wet state) and, after passage of 5 ml of a plasma from a rheumatoid patient at a flow rate of 0.3 ml/min. at a column temperature of 37° C., rheumatoid factor (IgG-RF) in the plasma was analyzed to obtain the results as shown in Table 3.

Rheumatoid factor was assayed by the ELISA method.

(c) After a system in which the body fluid purifying material No. 1 prepared as described above and a plasma from a systemic lupus erythematosus patient were at a volume ratio of 1:3 was incubated at 37° C. for 2 hours, anti-DNA antibody and immune complex in the plasma were analyzed to obtain the results as shown in Table 3.

Anti-DNA antibody was analyzed by the RIA (ammonium sulfate salting-out) method and immune complex by the EIA method.

(d) After a system in which the body fluid purifying material No. 1 prepared as described above and a plasma from a patient of Hashimoto's disease were at a volume ratio of 1:3 was incubated at 37° C. for the predetermined time as shown in Table 4, anti-thyroglobulin antibody and anti-thyroid microsome antibody in the plasma were analyzed to obtain the results as shown in Table 4.

Anti-thyroglobulin antibody and anti-thyroid microsome antibody were assayed by the particle agglomeration method.

(e) The same adsorption as the adsorption test (1) in Example 1 was conducted except that the body fluid purifying material No. 1 according to the present invention as prepared above was used as the body fluid purifying material and the total plasma passed was 30 ml, and TP, AL, IgG, anti-T-cell antibody and anti-B-cell in the plasma were assayed to obtain the results as shown in Table 5.

EXAMPLE 3

Preparation of body fluid purifying material

Body fluid purifying materials were prepared in the same manner as in Example 2 except for changing the amounts of HMDI charged and DMSO during the reaction between Sepharose Cl-4B and HMDI as shown in Table 3, and called body fluid purifying materials No 2, 3, 4, 5, 6, 7, 8, 9 and 10. These materials contained nitrogen contents as shown in Table 3.

Adsorption test

In place of the body fluid material prepared in Example 2, the body fluid purifying materials No. 2, 3, 4, 5, 6, 7, 8, 9 and 10 prepared as described above were used, and the adsorption tests were conducted under otherwise the same conditions as in the adsorption tests (a), (b) and (c), to give the results as shown in Table 3.

EXAMPLE 4

Preparation of body fluid purifying material

A cross-linked agarose [trade name: Sepharose CL-4B, produced by Pharmacia Co.] was washed repeatedly with distilled water, and water was completely squeezed off by suction filtration. An amount of 30.0 g of the crosslinked agarose under wet state (2.0 g under absolutely dry state) was added into 80 ml of DMSO and the mixture was stirred at ambient temperature for 1 hour After DMSO was removed in a system in absence of moisture, 50 ml of dehydrated DMSO was freshly added, followed by repetition of similar operations. When the water content in the DMSO in the system became 50 ppm or less, a solution of 1.4 g of HMDI added into 15 ml of dehydrated DMSO was charged into this system, and the reaction was carried out at 100 ° C for 1.5 hours under stirring (the amount of DMSO in the reaction system was 65 ml). After removal of the reaction solvent, 100 ml of fresh DMSO was charged and washing was performed by stirring at ambient temperature for 1 hour. Subsequently, washing was repeated until the isocyanate in DMSO in the system became $1 \times 10^{-6}$ equivalent or less by titration analysis. The reaction product was washed with a large amount of distilled water and confirmed to be free from eluted product, followed by sterilization by high pressure steam at 121° C. for 30 minutes.

The water-insoluble polymeric compound thus prepared was suction filtered and provided for the following test as body fluid purifying material No. 11. The water containing water-insoluble polymeric compound suction filtered was found to have a water content of 69.2%, and the dried product thereof had a nitrogen content of 5.11%.

Adsorption test

The same adsorption tests as the adsorption tests (a), (b) and (c) in Example 2 were conducted except for using the body fluid purifying materials as prepared above in place of the body fluid purifying material prepared in Example 2 to give the results shown in Table 3.

EXAMPLE 5

Preparation of body fluid purifying material

An amount of 15 g of a dry polyvinyl alcohol (polymerization degree: about 1,500), 3 g of Desmodur R (20% by weight methylene chloride solution of triphenylmethane-4,4',4''-triisocyanate; Bayer A. G.) and 50 ml of dehydrated DMSO were charged into a flask equipped with a stirring means, and the reaction was carried out under stirring at 110° C. for 2 hours. The reaction mixture was added into water, and the precipitates were collected, washed successively with water and ethanol, and then subjected to Soxhlet extraction with water and with ethanol each for 24 hours. After extraction, the residue was made the body fluid purifying material and provided for the following test. The dried product of the residue after extraction was found to have a nitrogen content of 8.21%.

The product prepared according to the above method is called body fluid purifying material J.

Adsorption test

Except for using the body fluid purifying material as prepared above as the body fluid purifying material, the same adsorption test as the adsorption test (3) in Example 1 was conducted to obtain the results as shown below.

|  | TP (g/dl) | AL (g/dl) | IgG (mg/dl) |
|---|---|---|---|
| Before the present adsorption test | 6.3 | 4.3 | 1623 |
| After the present adsorption test | 5.5 | 4.0 | 1280 |

TABLE 3

| Body fluid purifying material of the present invention | | Example 2 | Example 3 | | | | | | | | | Example 4 |
|---|---|---|---|---|---|---|---|---|---|---|---|---|
| | | 1 | 2 | 3 | 4 | 5 | 6 | 7 | 8 | 9 | 10 | 11 |
| Preparation conditions | Amount of HMDI (g) | 2.28 | 4.45 | 4.45 | 4.45 | 4.45 | 2.28 | 2.28 | 6.73 | 6.73 | 6.73 | 1.4 |
| | Amount of DMSO* (ml) | 125 | 50 | 125 | 200 | 300 | 50 | 200 | 200 | 300 | 500 | 65 |
| Nitrogen content in water-insoluble polymeric substance prepared (%) | | 4.68 | 7.13 | 7.15 | 5.41 | 4.26 | 5.71 | 3.95 | 5.63 | 4.67 | 3.97 | 5.11 |
| Adsorption test | (a) IgG adsorption rate (%) | 65.9 | 53.5 | 58.3 | 55.9 | 56.7 | 62.3 | 51.0 | 60.2 | 54.1 | 50.6 | 33.5 |
| | AL adsorption rate (%) | 7.8 | 13.8 | 13.5 | 17.2 | 16.1 | 10.4 | 12.2 | 17.8 | 13.0 | 11.3 | 18.9 |
| | TP adsorption rate (%) | 24.1 | 20.5 | 22.6 | 26.9 | 24.1 | 22.3 | 18.1 | 21.5 | 24.0 | 26.1 | 24.3 |
| | (b) Rheumatoid adsorption rate (%) | 81.1 | 56.5 | 58.2 | 70.3 | 75.1 | 78.3 | 69.4 | 79.1 | 73.0 | 60.1 | 59.8 |
| | (c) Anti-DNA adsorption rate (%) | 76.2 | 60.5 | 65.7 | 67.8 | 73.2 | 75.5 | 70.3 | 74.2 | 71.5 | 68.2 | 62.3 |
| | Immune complex adsorption rate (%) | 63.2 | — | — | — | — | — | — | — | — | — | — |

*DMSO amount in the system during reaction between Sepharose CL-4B and HMDI.

TABLE 4

| Adsorption time | TP (g/dl) | AL (g/dl) | IgG (mg/dl) | *Anti-thyroglobulin antibody | *Anti-thyroid microsome antibody |
|---|---|---|---|---|---|
| 0 min | 7.4 | 4.2 | 1784 | 800-fold | 25600-fold |
| 30 min | 6.2 | 4.0 | 920 | 200-fold | 6400-fold |
| 120 min | 6.2 | 4.0 | 845 | 200-fold | 6400-fold |

*dilution

TABLE 5

| Kind of fluid purifying material | Amount of body fluid purifying material [ml (wet)] | Plasma circuration time (min) | TP (g/dl) | AL (g/dl) | IgG (mg/dl) | Anti-T-cell antibody* | | | Anti-B-cell antibody* | | |
|---|---|---|---|---|---|---|---|---|---|---|---|
| | | | | | | 5° C. | room temperature | 37° C. | 5° C. | room temperature | 37° C. |
| — | None | 0 | 5.9 | 4.5 | 612 | 8 | 8 | 8 | 8 | 8 | 8 |
| | | | | | | 8 | 8 | 8 | 8 | 8 | 8 |
| — | None | 120 | 5.9 | 4.5 | 612 | 8 | 8 | 8 | 8 | 8 | 8 |
| | | | | | | 8 | 8 | 8 | 8 | 8 | 8 |
| J | 3 | 60 | 5.3 | 4.1 | 182 | 1 | 1 | 1 | 8 | 8 | 1 |
| | | | | | | 1 | 1 | 1 | 8 | 8 | 1 |
| | 3 | 120 | 5.2 | 4.1 | 165 | 1 | 1 | 1 | 8 | 8 | 1 |
| | | | | | | 1 | 1 | 1 | 8 | 8 | 1 |
| | 5 | 60 | 4.9 | 3.9 | 154 | 1 | 1 | 1 | 8 | 8 | 1 |
| | | | | | | 1 | 1 | 1 | 8 | 8 | 1 |
| | 5 | 120 | 4.7 | 3.8 | 132 | 1 | 1 | 1 | 8 | 8 | 1 |
| | | | | | | 1 | 1 | 1 | 8 | 8 | 1 |

*representation of score by CDC test.
1: 0 to 10% killed, 2: 11 to 20% killed, 4: 21 to 40% killed, 6: 41 to 80% killed and 8: 81 to 100% killed.

EXAMPLE 6

A glass column of 10 mm inner diameter was filled with the adsorbent I obtained in Example 1 and equipped at the inlet and outlet with filters of 20 micron mesh. The blood employed was sampled from a patient after kidney transplantation. The total amount of blood passed through the adsorption test apparatus was 20 ml, with the circulation rate of blood being 0.2 ml/min, and the column temperature being 37 ° C. After circulation for 120 minutes, the plasma was separated and Tp, AL, IgG, anti-T-cell antibody and anti-B-cell antibody were analyzed similarly as in Example 1. The results are shown in Table 6.

TABLE 6

| Kind of fluid purifying material | Amount of body fluid purifying material [ml (wet)] | Plasma circuration time (min) | TP (g/dl) | AL (g/dl) | IgG (mg/dl) | Anti-T-cell antibody* | | | Anti-B-cell antibody* | | |
|---|---|---|---|---|---|---|---|---|---|---|---|
| | | | | | | 5° C. | room temperature | 37° C. | 5° C. | room temperature | 37° C. |
| — | None | 0 | 6.1 | 5.1 | 625 | 8 | 8 | 8 | 8 | 8 | 8 |
| | | | | | | 8 | 8 | 8 | 8 | 8 | 8 |
| — | None | 120 | 6.1 | 5.1 | 625 | 8 | 8 | 8 | 8 | 8 | 8 |
| | | | | | | 8 | 8 | 8 | 8 | 8 | 8 |
| I | 5 | 120 | 5.6 | 4.6 | 220 | 1 | 1 | 1 | 8 | 8 | 1 |
| | | | | | | 1 | 1 | 1 | 8 | 8 | 1 |

*representation of score by CDC test.
1: 0 to 10% killed, 2: 11 to 20% killed, 4: 21 to 40% killed, 6: 41 to 80% killed and 8: 81 to 100% killed.

By use of the body fluid purifying material of the present invention, only unnecessary factors in body fluid (such as blood, etc.,) can be selectively removed.

Further, according to the removing method of the present invention, anti-T-cell antibody can be easily and effectively removed, and consequently, rejection reactions accompanied with organ transplantation can be inhibited or alleviated.

I claim:

1. A material for removing immunoglobulins, IgG of multiple myeloma patient, immune complexes or rheumatoid factors from blood or plasma, comprising a water-insoluble compound obtained by reacting
   one or more compounds having hydroxyl groups and being selected from the group consisting of agarose, cellulose, dextran, chitin, chitosan, and polyvinyl alcohol with
   a compound having at least one isocyanate group and selected from the group consisting of hexamethylene diisocyanate and tetramethylene diisocyanate;
   at 10° to 200° C., with a molar ratio of —NCO/—OH of 1 or more; and then
   treating with an amine, an alcohol or water at 10° to 200° C. while stirring thereby to deactivate unreacted isocyanate groups which may be present and form said material with a nitrogen content under dry state of 3.0 to 8.0% by weight when deactivated with water or alcohol, or a nitrogen content of 3.5 to 9.0% by weight when deactivated with amine.

2. A method for removing anti-T-cell antibodies from blood or plasma containing said antibodies, which comprises contacting the blood of an organ transplantation patient or the plasma separated from said blood with an adsorbent, thereby adsorbing and removing anti-T-cell antibody, and thereafter removing the blood from contact with adsorbent; and wherein the adsorbent comprises a product obtained by reacting a water-insoluble polymeric compound having hydroxyl groups selected from the group consisting of agarose, cellulose, dextran, chitin, chitosan, and polyvinyl alcohol
   wherein the compound having at least one isocyanate group is at least one of hexamethylene diisocyanate and tetramethylene diisocyanate.

3. The method according to claim 2, wherein the anti-T-cell antibody is anti-T-warm antibody.

4. The method according to claim 2, wherein the adsorbent is filled in a column and the blood or the plasma is passed through said column.

* * * * *